United States Patent [19]

Yozu

[11] Patent Number: 4,994,017
[45] Date of Patent: Feb. 19, 1991

[54] CIRCULATION APPARATUS
[75] Inventor: Ryohei Yozu, Yokohama, Japan
[73] Assignee: Toyo Boseki Kabushiki Kaisha, Osaka, Japan
[21] Appl. No.: 393,985
[22] Filed: Aug. 15, 1989
[30] Foreign Application Priority Data
  Sep. 28, 1988 [JP] Japan .................... 63-242690
[51] Int. Cl.⁵ .................................. A61M 1/12
[52] U.S. Cl. ..................................... 600/16
[58] Field of Search .......................... 600/16, 17
[56] References Cited
   U.S. PATENT DOCUMENTS
   4,135,253  1/1979  Reich et al. ............. 600/16
   4,375,941  3/1983  Child ...................... 600/16
   4,524,466  6/1985  Hall et al. ............... 600/16
   4,625,712 12/1986  Wampler ................. 128/10

OTHER PUBLICATIONS

"A Compact Centrifugal Blood Pump for Extracorporeal Circulation: Design and Performance", Tanaka et al., Transactions of ASME, vol. 109, Aug. 1987.

Primary Examiner—William E. Kamm
Assistant Examiner—Scott M. Getzow
Attorney, Agent, or Firm—Leydig, Voit & Mayer

[57] ABSTRACT

A circulation apparatus with a compact construction and high reliability comprising a ring-shaped support frame which has a joint which can be connected in the vascular system and turbine blades mounted on the support frame which can be rotated by a drive source, thereby attaining an easy installation thereof on the heart without exerting pressure on other organs and without causing thrombus.

7 Claims, 4 Drawing Sheets

CIRCULATION APPARATUS

BACKGROUND OF THE INVENTION

1. Field of the invention

This invention relates to a circulation apparatus and, more particularly, relates to a circulation apparatus which is capable of compensating for or supplementing the function of a heart to circulate the blood.

2. Description of the prior art

In the area of artificial organs, especially artificial hearts, various proposals have been made or put into practical use in recent years.

As a circulation apparatus which supplements the blood circulating function of a heart with deteriorated blood circulating abilities, for example, an apparatus which utilizes an air compressor coupled to a diaphragm pump, pusher plate pump or the like has become commercially available.

However, in a conventional circulation apparatus which uses a diaphragm pump as shown in FIG. 5, a compressor must be installed outside the body to supply air (indicated by arrow A in the drawing) in the casing a or exhaust the air (indicated by arrow A' in the drawing) from the casing a in order to drive a diaphragm b (directions of the movements are indicated by B and B' in the drawing), and the pump and the compressor must be connected. Installation of such a circulation apparatus on a patient's body causes substantial restriction on the patient's body movement.

On the other hand, in another conventional apparatus which comprises a pusher plate c as shown in FIG. 6, a compliance chamber is required to accommodate the changes of the inner volume of the casing e accompanying the vertical movement of the piston d (directions of the movements are indicated by D and D' in the drawing) which drives the pusher plate c (directions of the movements are indicated by C and C' in the drawing). If a circulation apparatus of such a constitution as described above is to be planted in a human body, a space must be made in the body to accommodate the pump h and the compliance chamber i, each having a bypass passage g made of an artificial blood vessel, with the bypass passage g sutured to the heart j, for example, as shown in FIG. 7. This results in a problem of the pump h and the compliance chamber i exerting pressure on other organs.

In both FIG. 5 and FIG. 6, the reference numeral f denotes a valve.

These conventional circulation apparatuses have other problems such that the bypass blood passages required in every case makes the surgery of connecting the apparatus to the heart extremely difficult and that complexity of the apparatus construction results in poor reliability of the apparatus and that large area of contact with blood leads to great probability of causing thrombus.

SUMMARY OF THE INVENTION

In order to resolve the problems mentioned above, the inventor conducted an extensive research which resulted in a circulation apparatus of a particular constitution where a turbine blade rotated by a drive source is installed on a support frame, having advantages as follows:

The circulation apparatus is compact, has a simple construction and high reliability. The circulation apparatus can be installed to a heart easily without exerting pressure on other organs or causing thrombus. The circulation apparatus can be preferably used either in a case where it is intended to compensate for the lost ability of the heart to circulate the blood, or in a case where it is intended to support the blood circulation function when the ability of the heart to circulate the blood is deteriorated.

The circulation apparatus of this invention, which overcomes the above-discussed and numerous other disadvantages and deficiencies of the prior art, comprises a ring-shaped support frame having a joint which can be connected in the vascular system and turbine blades mounted on the support frame which can be rotated by a drive source.

In a preferred embodiment, the ring-shaped support frame comprises a support pillar that supports said drive source and a housing that rotatably supports the end of a rotary shaft bearing said turbine blades and that protects said turbine blades, said joint being provided on said housing.

In a preferred embodiment, the vascular system includes the main artery and large vessel directly connected to the heart, cardiac valve ring, or artificial vessel, etc.

In a preferred embodiment, connection of said vascular system and said joint is achieved by suturing.

In a preferred embodiment, the circulation apparatus is used as a so-called complete artificial heart to take over the blood circulating function of a heart when its blood circulating ability is lost, or as an auxiliary circulation apparatus to assist the blood circulating function of a heart when its blood circulating ability is deteriorated.

Thus, the invention described herein makes possible the objective of providing a circulation apparatus of a compact construction and high reliability which can be easily installed in the vascular system and does not exert pressure on other organs nor causes thrombus.

BRIEF DESCRIPTION OF THE DRAWINGS

This invention may be better understood and its numerous objects and advantages will become apparent to those skilled in the art by reference to the accompanying drawings as follows.

DESCRIPTION OF THE PREFERRED EMBODIMENTS

This invention provides a circulation apparatus that is installed in a vascular system by connecting the joint section provided along the periphery of the ring-shaped support frame in the vascular system. When the circulation apparatus is installed in the vascular system and the turbine blade is rotated by a drive source, forced blood circulation is attained.

Figure 1:
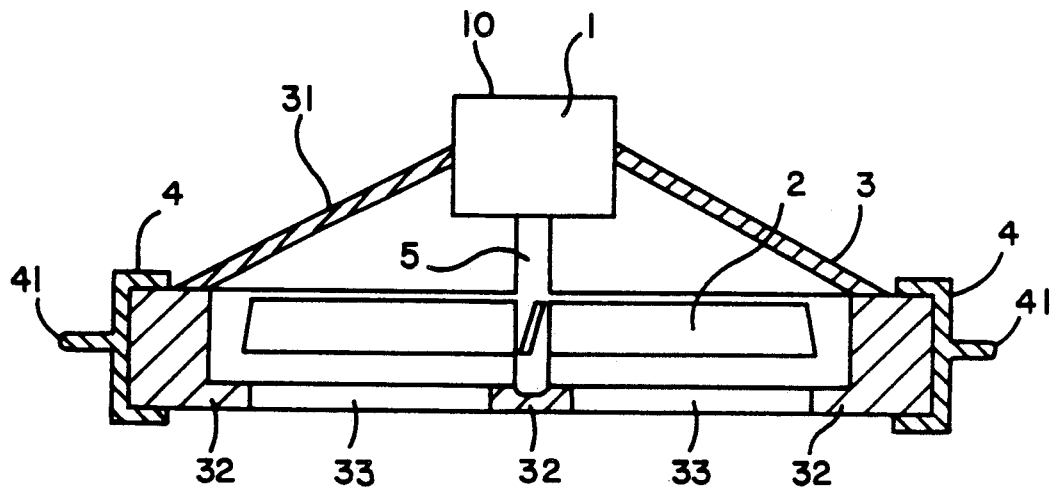
FIG. 1 is a sectional view showing a part of a circulation apparatus of this invention.

FIG. 1 shows a circulation apparatus of this invention, which comprises a drive source 1, turbine blades 2, ring-shaped support frame 3 and a joint 4.

The drive source 1 is composed, for example, of a motor (not shown) and a casing 10 which houses the motor.

As the power source in case a motor is used for the drive source 1, for example, an embedded rechargeable battery can preferably be used. Otherwise a battery can be installed outside the body, and a motor can be mounted on the drive source 1.

The casing 10 constituting the drive source 1 is made of such a material that has antithrombophilic properties and does not cause electrolysis or ionization, or can be coated with such a material on the surface thereof.

The material to make the casing body can be pyrolite carbon, for example. The material to coat the surface of the casing 10 can be polyurethane for medical use or the like.

Figure 2:
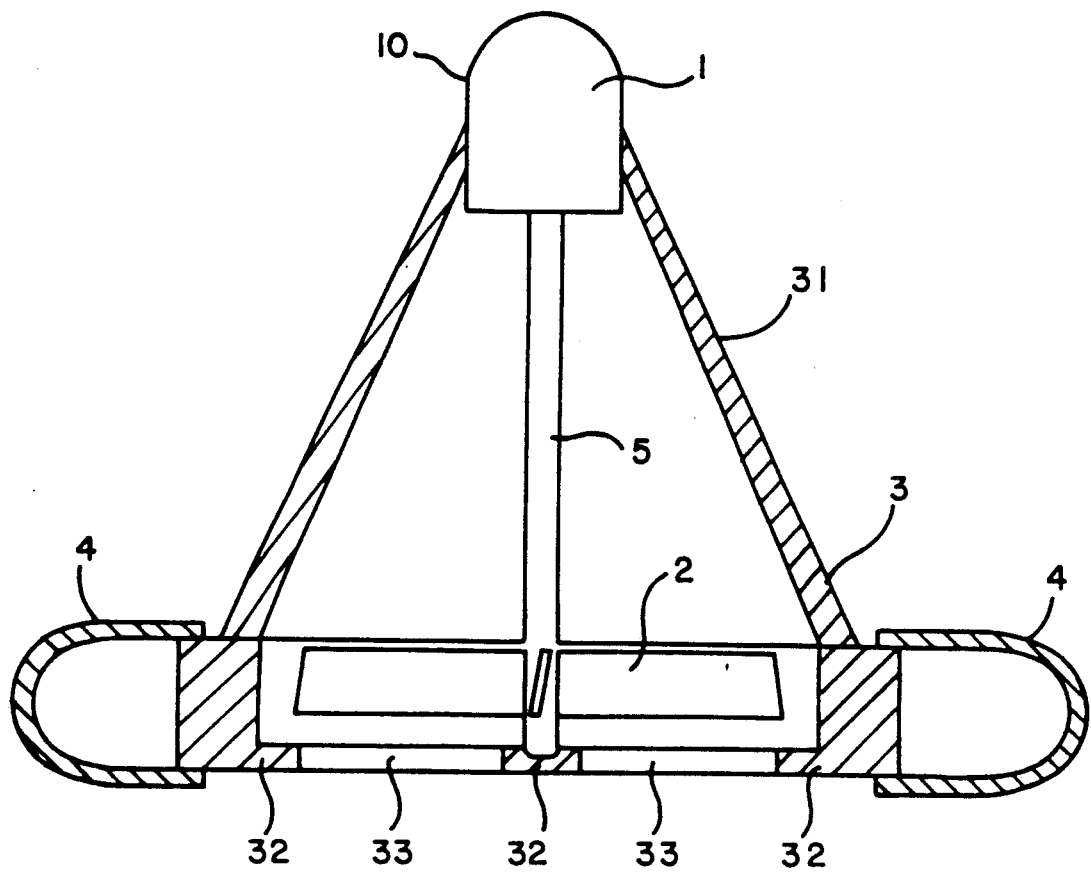
FIG. 2 is a sectional view showing a part of another circulation apparatus of this invention.

Although the casing 10 can be made in a cylindrical shape as shown in FIG. 1, it is preferably made in an aerodynamic configuration as shown in FIG. 2 in order to achieve smooth blood flow.

The circulation apparatus of the embodiment is provided with a turbine blade 2 mounted on a rotary shaft 5 of the drive source 1. In FIG. 1 and FIG. 2, the turbine blade is illustrated with smaller number of blades for the sake of simplicity.

As the rotary shaft 5 of the drive source 1 rotates, the turbine blade 2 rotates in the heart, blood vessel or artificial blood vessel to accelerate the blood flow thereby to compensate for or supplement the blood circulation function of the heart.

Rotation of the turbine blade 2 can be controlled by means of a control mean which is connected to the drive source 1 or built therein, to provide for control in accordance with the predetermined total quantity of blood flow, artery blood pressure, left atrium pressure and right atrium pressure.

In particular, pulsating blood pressure can be formed by adjusting the revolution speed of the turbine blade 2 by means of the control section periodically or through sensing the electrocardiograph signals, or steady blood flow can be achieved by maintaining the rotation of the turbine blade constant. The control by the control section can be achieved by means of ICs (Integrated Circuits) and LSIs (Large Scale Integrated Circuits). The control section can be installed outside of the body or mounted on the circulation apparatus.

The end of the rotary shaft 5 which bears the turbine blade 2 and the drive source 1 are supported by the ring-shaped support frame 3.

Consequently, as shown in FIG. 1 and FIG. 2, the ring-shaped support frame 3 is composed, for example, of a support pillar 31 which supports the drive source 1 and a housing 32 which rotatably supports the end of the rotary shaft 5 while protecting the turbine blades 2.

The housing 32 has holes 33 to secure the passage for blood flow. As a result, in this embodiment, rotation of the turbine blade 2 by means of the drive source 1 causes a blood flow, for example, from the drive source side to the holes 33.

The support pillar 31 and the housing 32 which constitute the ring-shaped support frame 3 are preferably made of materials which have antithrombophilicity as well as high hardness and elasticity, and which does not wear while supporting the end of the rotary shaft 5 rotatably. As such a material, pyrolite carbon can be used.

On the periphery of the housing 32 of the ring-shaped support frame 3, the joint 4 is provided as shown in FIG. 1 and FIG. 2.

The joint 4 is the part which is sutured to the heart valve ring, blood vessel or artificial blood vessel under the condition that it is in contact with the inner wall of the heart valve ring, blood vessel or artificial blood vessel, and can be formed by using a textile such as Dacron and Teflon (both trade marks).

The joint 4 can be constructed either in a shape which has a flange 41 as shown in FIG. 1 or in a shape which is curved protruding at the center as shown in FIG. 2. In either case, the cross section of the joint 4 is preferably so shaped as to allow suture thread to pass easily.

The circulation apparatus of the invention can be used either as a so-called complete artificial heart to take over the blood circulating function of a heart when its blood circulating ability is lost, or as an auxiliary circulation apparatus to assist the blood circulating function of a heart when its blood circulating ability is deteriorated.

Figure 3:
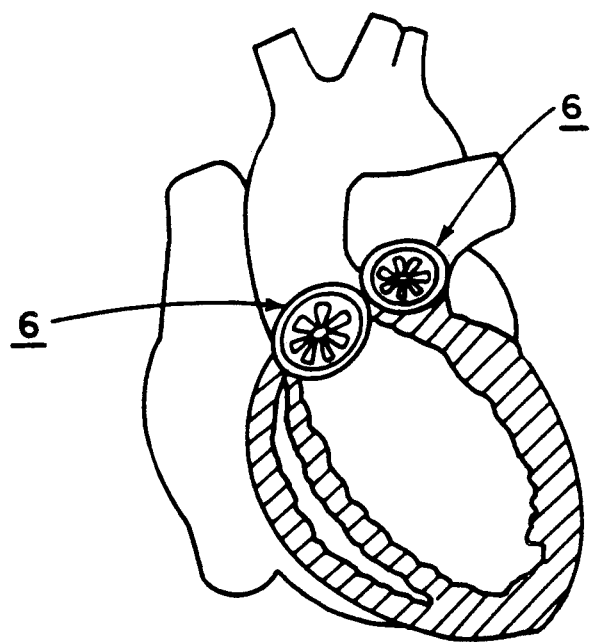
FIGS. 3 and 4, respectively, are schematic diagrams showing the installation of the circulation apparatuses of this invention into the human body.
Figure 4:
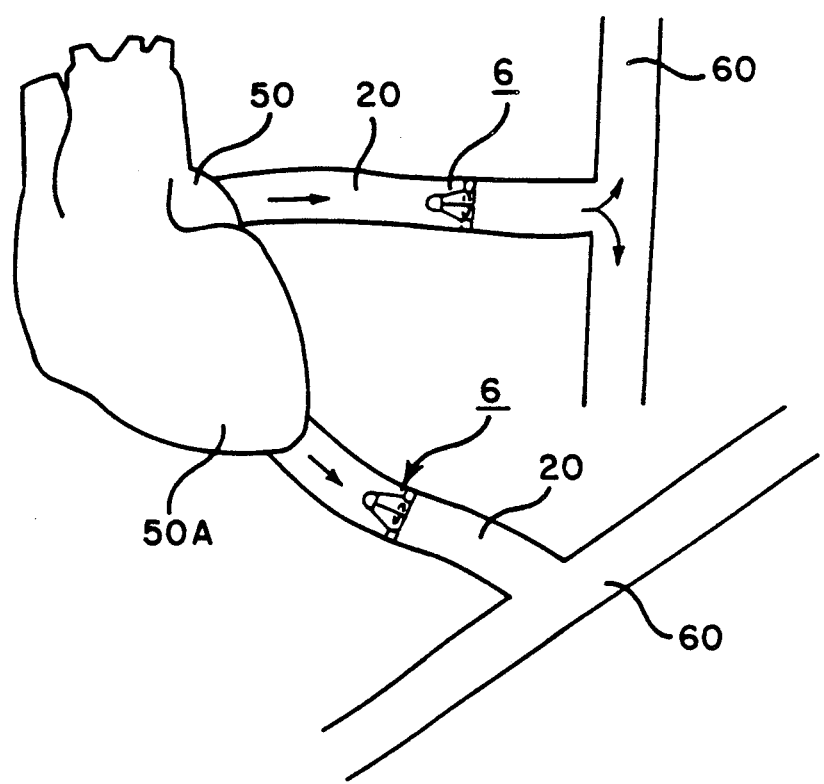
Figure 5:
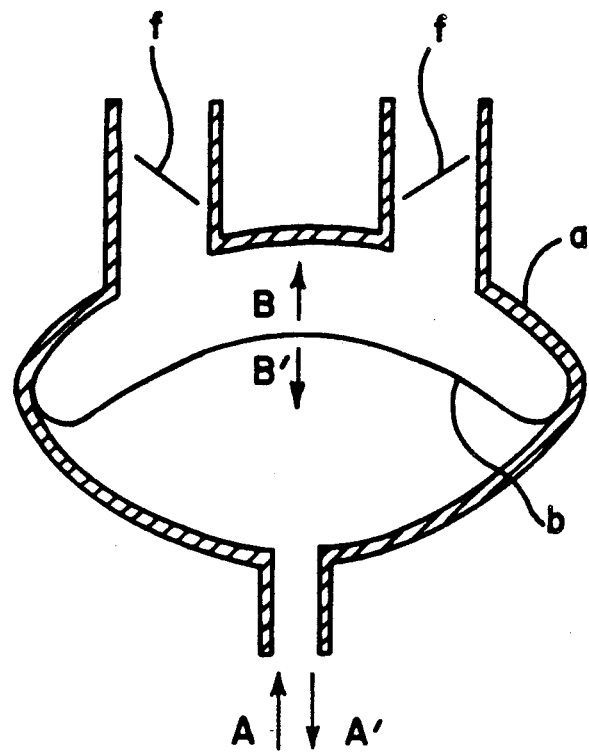
FIGS. 5 and 6, respectively, are sectional views showing conventional circulation apparatuses.
Figure 6:
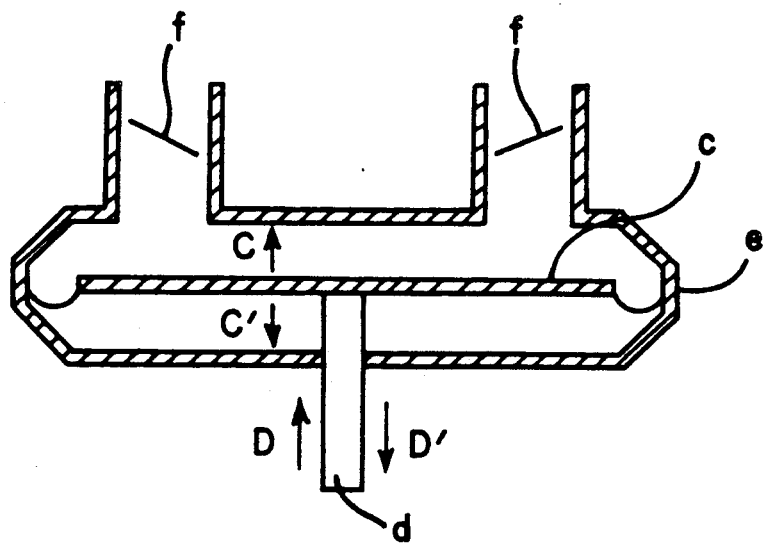
Figure 7:
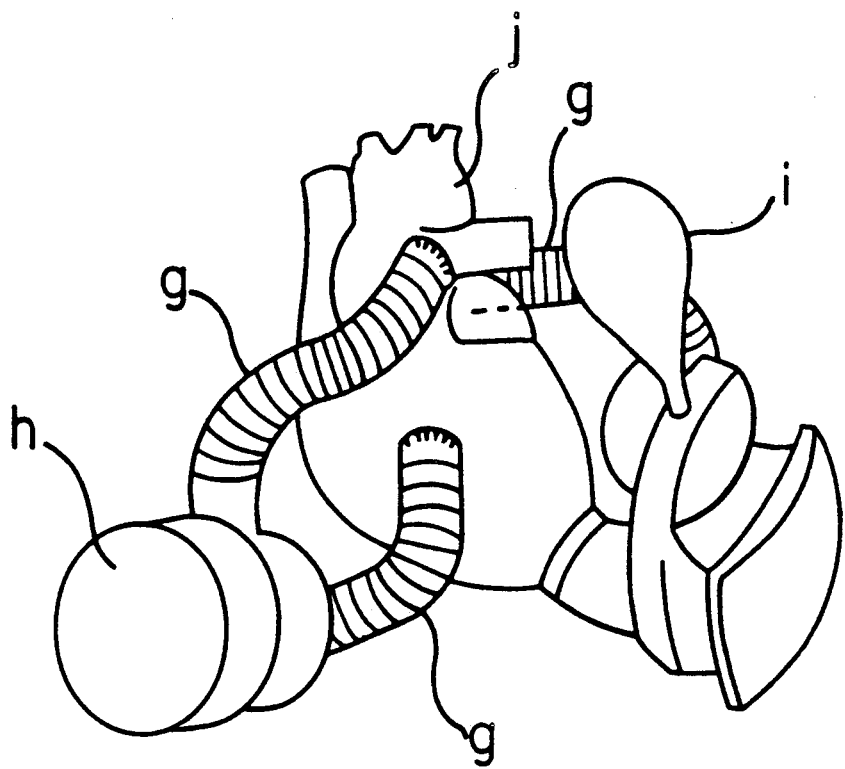
FIG. 7 is a schematic diagram showing the installation of conventional circulation apparatuses into a human body.

When used as a complete artificial heart, for example, as shown in FIG. 3, circulation apparatuses 6 of the invention can be installed in the main artery valve ring and the pulmonary artery of the heart, respectively. The circulation apparatus can also be installed in the mitral valve and tricuspidal valve ring. Moreover, when the circulation apparatus of the invention is installed in at least one of the main artery valve rings, the pulmonary artery, the mitral valve and tricuspidal valve ring of the heart, for example, the circulation apparatus can be used as an auxiliary circulation apparatus to maintain the normal blood circulation function of the heart.

It should be noticed, however, when a plurality of the circulation apparatuses of the invention are used in one patient, that the circulation apparatuses are preferably operated while being linked to each other through electrocardiographic synchronization.

On the other hand, when the circulation apparatus is used temporarily as an auxiliary circulation apparatus in the case of heart surgery, particularly after the surgery, the circulation apparatus 6 of the invention can be installed in an artificial blood vessel 20 with an end of the artificial blood vessel 20 connected to the left atrium 50 or to the left ventricle (apex cordis) 50A, and another end connected to the main artery 60, so that the circulation apparatus 6 causes blood flow from the left atrium 50 or the left ventricle (apex cordis) 50A to the main artery 60.

In either case, rotation of the turbine blade 2 can be at a constant speed or at variable speeds to achieve pulsation, as described previously.

In accordance with this invention, a circulation apparatus can be provided which has various advantages such as;

(1) High reliability due to compact and simple construction, (2) Being less likely to cause thrombus due to less area of contact with blood, (3) Applicability either as a so-called complete artificial heart to take over the blood circulating function of a heart when its blood circulating ability is lost, or as an auxiliary circulation apparatus to recover the blood circulating function of a heart to the normal range when its blood circulating function is deteriorated, and (4) Capability of being installed by a surgical technique similar to surgery to replace damaged valves with artificial ones which are normally conducted in the area of heart surgery, thereby allowing easy installation without exerting pressure on other organs.

It is understood that various other modifications will be apparent to and can be readily made by those skilled in the art without departing from the scope and spirit of this invention. Accordingly, it is not intended that the scope of the claims appended hereto be limited to the description as set forth herein, but rather that the claims be construed as encompassing all the features of patentable novelty that reside in the present invention, including all features that would be treated as equivalents thereof by those skilled in the art to which this invention pertains.

What is claimed is:

1. An apparatus for circulating fluids within a vascular system, said system having inner walls, comprising
   a support frame having a cavity for directing flow axially of the frame and adapted for fixation onto an inner wall of said vascular system,
   turbine blades rotatably mounted to said support frame in said cavity which are adapted for applying a driving force to the fluid such that axial fluid movement is produced, and
   means for rotating said blades, said means being mounted upon said support frame and residing within the vascular system, said apparatus residing within the vascular system.

2. The apparatus of claim 1, wherein said rotating means further comprises a means for controlling the speed of said rotating means such that said rotating means is adapted for rotating said blades to produce pulsating fluid flow.

3. The apparatus of claim 1, wherein said support frame is generally ring-shaped.

4. The apparatus of claim 1, wherein said support frame further comprises a joint, said joint being mounted onto said support frame such that said joint is adapted for fixation onto the inner wall of the vascular system.

5. The apparatus of claim 1, further comprising a means for regulating the speed of said blade rotating means.

6. A device for circulating fluids through a vascular system, said system having inner walls, comprising
   a plurality of circulation apparatuses, each of which comprising
   a support frame having a cavity for directing flow axially of the frame and adapted for fixation onto an inner wall of said vascular system,
   turbine blades rotatably mounted to said support frame in said cavity which are adapted for applying a driving force to the axial fluid such that fluid movement is produced, and
   means for rotating said blades, said means being mounted upon said support frame,
   each of said circulation apparatuses residing within the vascular system and
   control means adapted for simultaneously and individually regulating the speed of said individual blade rotating means.

7. A method for circulating fluids through a vascular system, said system having inner walls, comprising
   providing a plurality of circulation apparatuses, each of which comprising a support frame having a cavity for directing flow axially of the frame and adapted for fixation onto an inner wall of said vascular system, turbine blades rotatably mounted to said support frame which are adapted for applying a driving force to the fluid such that axial fluid movement is produced, and means for rotating said blades, said means being mounted upon said support frame, each of said circulation apparatuses residing within the vascular system and
   controlling the speed of said individual blade rotating means.

* * * * *

UNITED STATES PATENT AND TRADEMARK OFFICE
CERTIFICATE OF CORRECTION

PATENT NO. : 4,994,017
DATED : February 19, 1991
INVENTOR(S) : Ryohei Yozu

It is certified that error appears in the above-identified patent and that said Letters Patent is hereby corrected as shown below:

Column 6, line 15, delete the word "axial" and add "axial" after the word -- that --.

Signed and Sealed this

Twentieth Day of June, 1995

BRUCE LEHMAN

*Attest:*

*Attesting Officer*          *Commissioner of Patents and Trademarks*